US007786170B2

(12) United States Patent
Bhalla

(10) Patent No.: US 7,786,170 B2
(45) Date of Patent: Aug. 31, 2010

(54) HISTONE DEACETYLASE INHIBITOR ENHANCEMENT OF TRAIL-INDUCED APOPTOSIS

(75) Inventor: Kapil N. Bhalla, Tampa, FL (US)

(73) Assignee: University of South Florida, Tampa, FL (US)

( * ) Notice: Subject to any disclaimer, the term of this patent is extended or adjusted under 35 U.S.C. 154(b) by 544 days.

(21) Appl. No.: 11/147,112

(22) Filed: Jun. 6, 2005

(65) Prior Publication Data

US 2007/0207119 A1    Sep. 6, 2007

Related U.S. Application Data

(63) Continuation of application No. PCT/US2003/038881, filed on Dec. 8, 2003.

(60) Provisional application No. 60/319,759, filed on Dec. 6, 2002.

(51) Int. Cl.
*A61K 31/19* (2006.01)
*A61K 38/00* (2006.01)

(52) U.S. Cl. ............... 514/575; 514/2; 514/908

(58) Field of Classification Search ............ 514/575, 514/908, 2
See application file for complete search history.

(56) References Cited

U.S. PATENT DOCUMENTS

| 5,763,223 | A |   | 6/1998 | Wiley et al. |
| 5,858,024 | A | * | 1/1999 | De Lacharriere et al. ....... 8/408 |
| 6,284,236 | B1 | * | 9/2001 | Wiley et al. ................ 424/85.1 |
| 2005/0096468 | A1 | * | 5/2005 | Van Emelen et al. ......... 544/238 |

FOREIGN PATENT DOCUMENTS

WO    02/22577 A2    3/2002

OTHER PUBLICATIONS

He et al., "Histone deacetylase inhibitors indue remission in transgenis models of therapy-resistant acute promyelocytic leukemia", The Journal of Clinical Investigation, vol. 108, No. 9, pp. 1321-1330 (Nov. 2001).*
Kosugi et al., "Histone deacetylase inhibitors are the potent inducer/enhancer of differentiation in acute myeloid leukemia: a new approach to anti-leukemia therapy", Leukemia, vol. 13, pp. 1316-1324 (1999).*
Fei Guo et al., Cotreatment with Histone Deacetylase Inhibitor LAQ824 Enhances Apo-2L, http://cancerres.aacrjournals.irg/cig/content/abstract/64/7/2580, Mar. 20, 2005.
Robert R. Rosato et al., Simultaneous Activation of the Intrinsic and Extrinsic Pathways by Histone Deacetylase Inhibitors, Moleclar Cancer Therapeutics, 2003, p. 1273-1284.
Sonnemann et al., "Histone deacetylase inhibitors interact synergistically with tumor necrosis factor-related apoptosis-inducing ligand (TRAIL) to induce apoptosis in carcinoma cell lines," Investigational New Drugs, 2005, 99-109, 23.
Remiszewski et al., "N-Hydroxy-3-phenyl-2-propenamides as Novel Inhibitors of Human Histone Deacetylase with in Vivo Antitumor activity: Discovery of (2E)-N-Hydroxy-3-[4-[[(2-hydroxyethyl)[2-(1H-indol-3-yl)ethyl]amino]methyl]-phenyl]-2-propenamide (NVP-LAQ824)," J. Med. Chem 2003, 4609-4624, 46.
Guo et al., "Co-treatment with histone deacetylase inhibitors suberoylanilide hydroxamic acid (SAHA) enhances Apo-2L/TRAIL-induced death inducing signaling complex and apoptosis of human acute lymphoid leukemia cells," Proceedings of the American Association for Cancer Research Jul. 2003, 154, 44 (2nd ed.).
Rosato, et al., "Histone deacetylase inhibitors interact in a highly synergistic manner with TRAIL to induce mitochondrial damage and apoptosis in human leukemia cells," Proceedings of the American Association for Cancer Research, Mar. 2002, 701, 43.
Inoue, et al., "Histone deacetylase inhibitors sensitize human colonic adenocarcinoma cell lines to TNF-related apoptosis inducing ligand-mediated apoptosis," International Journal of Molecular Medicine, vol. 9, No. 5, 521-525 (2002).
Guo et al., "Cotreatment with Histone Deacetylase Inhibitor LAQ824 Enhances Apo-2L/Tumor Necrosis Factor-Related Apoptosis Inducing Ligand-Induced Death Inducing Signaling Complex Activity and Apoptosis of Human Acute Leukemia Cells," Cancer Research, 2004, 2580-2589, 64.
Mitsiades et al., "Molecular sequelae of histone deacetylase inhibition in human malignant B cells," Blood 2003, 4055-4062, 101.

* cited by examiner

*Primary Examiner*—Kevin Weddington
(74) *Attorney, Agent, or Firm*—Bryan Cave LLP

(57) ABSTRACT

Due to the poor long-term clinical outcome in the adult patients with several forms of acute leukemia novel treatment strategies are needed to overcome resistance and sensitize the leukemia blasts to the extrinsic and intrinsic pathway of apoptosis. Treatment with LAQ824 and Apo-2L/TRAIL alone has been recognized to induce apoptosis of leukemia blasts but intrinsic mechanisms of resistance limit the antileukemia activity of either agent when administered alone. The inventive method overcomes the resistance to current apoptosis inducing treatments demonstrated by AML and CML-BC cells by concomitantly administering Apo-2L/TRAIL with the histone deacetylase inhibitor LAQ824.

5 Claims, 12 Drawing Sheets

A.

B.

B.

C.

|  | IP DNA / Input DNA | fold increase |
|---|---|---|
| Control | 0.06 | 1.0 |
| LAQ824 100 nM | 0.20 | 3.3 |
| LAQ824 200 nM | 0.34 | 5.7 |

A.

B.

SEQUENCE LISTING

<160> NUMBER OF SEQ ID NOS: 8

<210> SEQ ID NO 1
<211> LENGTH: 28
<212> TYPE: DNA
<213> ORGANISM: Artificial Sequence

```
<220> FEATURE:
<223> OTHER INFORMATION: Forward primer for DR5 promoter PCR.

<400> SEQUENCE: 1
ggaggaaaga gaaagagaga aaggaagg                                      28

<210> SEQ ID NO 2
<211> LENGTH: 24
<212> TYPE: DNA
<213> ORGANISM: Artificial Sequence
<220> FEATURE:
<223> OTHER INFORMATION: Reverse primer for DR5 promoter PCR.

<400> SEQUENCE: 2
ttgggggaaa tgagttgagg gagg                                          24

<210> SEQ ID NO 3
<211> LENGTH: 20
<212> TYPE: DNA
<213> ORGANISM: Artificial Sequence
<220> FEATURE:
<223> OTHER INFORMATION: Primer (dp1) used for p21WAF1 analysis.

<400> SEQUENCE: 3
ggtgtctagg tgctccaggt                                               20

<210> SEQ ID NO 4
<211> LENGTH: 16
<212> TYPE: DNA
<213> ORGANISM: Artificial Sequence
<220> FEATURE:
<223> OTHER INFORMATION: Primer (up1) used for p21WAF1 analysis.

<400> SEQUENCE: 4
tgtctaggtg ctccag                                                   16

<210> SEQ ID NO 5
<211> LENGTH: 20
<212> TYPE: DNA
<213> ORGANISM: Artificial Sequence
<220> FEATURE:
<223> OTHER INFORMATION: Forward primer for the c-FLIP PCR.

<400> SEQUENCE: 5
gcccgagcac cgagactacg                                               20

<210> SEQ ID NO 6
<211> LENGTH: 23
<212> TYPE: DNA
<213> ORGANISM: Artificial Sequence
<220> FEATURE:
<223> OTHER INFORMATION: Reverse primer for c-FLIP PCR.

<400> SEQUENCE: 6
agggacggdg agctgtgaga ctg                                           23

<210> SEQ ID NO 7
<211> LENGTH: 20
<212> TYPE: DNA
<213> ORGANISM: Artificial Sequence
<220> FEATURE:
<223> OTHER INFORMATION: beta-actin forward primer

<400> SEQUENCE: 7
ctacaatgag ctgcgtgtgg                                               20
```

-continued

```
<210> SEQ ID NO 8
<211> LENGTH: 20
<212> TYPE: DNA
<213> ORGANISM: Artificial Sequence
<220> FEATURE:
<223> OTHER INFORMATION: beta-actin reverse primer.

<400> SEQUENCE: 8
aaggaaggct ggaagagtgc                                              20
```

HISTONE DEACETYLASE INHIBITOR ENHANCEMENT OF TRAIL-INDUCED APOPTOSIS

CROSS REFERENCE TO RELATED APPLICATIONS

This application is a continuation of International Application No. PCT/US/2003/938881, filed on Dec. 8, 2003, which claims the benefit of U.S. Provisional Patent Application 60/319,759, filed Dec. 6, 2002, the contents of which are herein incorporated by reference.

FIELD OF INVENTION

This invention relates to an improved method for the treatment of leukemia.

BACKGROUND OF THE INVENTION

Tumor necrosis factor (TNF)-related apoptosis inducing ligand (TRAIL, also known as Apo-2L) is a member of the TNF family of cytokines that can bind and induce oligomerization of its agonistic cell-membrane death receptors TRAIL-R1 (DR4) and TRAIL-R2 (DR5). Upon binding and cross-linking by Apo-2L/TRAIL, or by agonistic antibodies, the death receptors DR4 and DR5 can trigger the activity of caspase-8 and apoptosis through the assembly of a cell-membrane associated multi-protein death inducing signaling complex (DISC). Although widely expressed in tissues, DR4 and DR5-mediated signaling for apoptosis is relatively selective for cancer cells, which has prompted the development of strategies to manipulate the levels and assembly of DISC components to ultimately increase caspase-8 activity. This, in turn, would either directly or through the recruitment of the mitochondria-based death machinery induce the processing and activity of the downstream effector caspases and apoptosis. An intracellular protein c-FLIP exists as two alternate spliced isoforms, c-FLIP$_L$ and c-FLIP$_S$. When recruited to the DISC through an interaction with the DED of FADD, c-FLIP$_L$ and c-FLIP$_S$ regulate the activation of caspase-8. c-FLIP competes with caspase-8 for binding to the DED of FADD and inhibits the activation of caspase-8. It is now well established that c-FLIP$_S$ inhibits Apo-2L/TRAIL-induced DISC and apoptosis. In contrast, although high c-FLIP$_L$ expression inhibits caspase-8 recruitment and activation, ectopic over-expression can induce apoptosis by interacting with and promoting the activation of caspase-8.

Active caspase-8 cleaves the cytosolic p22BID into the BH3-only domain-containing, proapoptotic, truncated p15 tBID fragment. tBID undergoes post-translational N-myristoylation to target the mitochondria, where it binds to its mitochondrial pro-apoptotic partner Bax or Bak to trigger the loss of mitochondrial membrane integrity. This results in the loss of a number of pro-death molecules from the mitochondria, including holocytochrome c, Omi and Smac (second mitochondria-derived activator of caspases) into the cytosol. Accordingly, BID may serve to amplify and link the extrinsic pathway to the mitochondrial events mediating triggering the intrinsic pathway of apoptosis. In the cytosol, cyt c and dATP bind to Apaf-1, which causes multimerization of Apaf-1, allowing the recruitment of procaspase-9 and -3 into an Apaf-1 assembled 'apoptosome.' This mediates the processing and activation of caspase-9 and -3, resulting in apoptosis. The processing and proteolytic activity of caspase-9, followed by caspases-3 and-7, is inhibited by the IAP (inhibitor of apoptosis) family of proteins, which includes XIAP, cIAP1, cIAP2 and survivin. All IAPs contain at least one BIR domain, although some contain three. In XIAP, another region, the RING domain, has ubiquitin ligase activity and promotes the self-degradation of XIAPs through the proteasomes in response to some apoptotic stimuli. Furthermore, during death receptor mediated apoptosis, XIAP is processed by activated caspase-3 into the amino-terminal BIR1-2 and BIR3-RING finger fragments. The latter specifically inhibits caspase-9. Overexpression of XIAP inhibits anticancer drug-induced caspase activity and apoptosis. In contrast, down-regulation of XIAP sensitizes cancer cells to apoptosis. The cytosolic accumulation of Smac and Omi relieves the inhibition of caspase-9 and -3 by XIAP by disrupting the interaction between BIR3 with caspase-9 and linker-BIR2 with caspase-3. Recently, the cytosolic Omi has been shown to cleave and inactivate IAPs. Taken together, the emerging evidence indicates that the pro-death molecules Smac and Omi by inactivating IAPs play an important regulatory role in Apo-2L/TRAIL-induced caspase activity and apoptosis.

Histone acetyltransferases (HATs) and histone deacetylases (HDACs) catalyze the acetylation and deacetylation of lysine residues in the core nucleosomal histone tails, respectively, which regulates the interaction affinity of the non-histone protein transcriptional complexes with DNA. Treatment with HDAC inhibitors (HDIs) causes hyperacetylation of the amino terminal lysine residues in the nucleosomal histones, and the histones that are associated with actively transcribed genes are highly acetylated. Exposure to HDIs, especially hydroxamic acid analogues, e.g., trichostatin A (TSA) and suberoylanilide hydroxamic acid (SAHA), have been demonstrated to induce p21$^{WAF1}$ (referred to as p21) and p27$^{KIP1}$ (referred to as p27), which is associated with cell cycle arrest and apoptosis of human leukemia cells, as well exert potent in vivo antileukemia effects. Recently, a cinnamic acid hydroxamate, LAQ824, has been demonstrated to act as a potent HDI at sub-micromolar levels. Through the present inventive method the effects of LAQ824 on molecular determinants of Apo-2L/TRAIL-induced DISC activity and signaling for apoptosis in human cultured and primary acute leukemia cells has been determined. Treatment with LAQ824 induces DR4 and DR5 but represses cFLIP levels, which is associated with increased Apo-2L/TRAIL-induced DISC activity. LAQ824 treatment also increased the mitochondrial release and cytosolic accumulation of pro-death molecules cyt c, Omi and Smac, resulting in increased activity of caspase-9 and -3 and apoptosis of human acute leukemia cells.

SUMMARY OF INVENTION

The inventive method therefore includes the steps of contacting a target cell with a therapeutic amount of tumor necrosis factor related apoptosis inducing ligand (trail), and concomitantly contacting the target cell with a therapeutic amount of a histone deacetylase inhibitor (hdi), wherein the histone deacetylase inhibitor is LAQ824.

Also included is a kit for the treatment of leukemia comprising tumor necrosis factor related apoptosis inducing ligand and a histone deacetylase inhibitor, wherein the histone deacetylase inhibitor is a hydromaxic acid analogue, and the hydromaxic acid analogue is LAQ824.

BRIEF DESCRIPTION OF THE DRAWINGS

For a fuller understanding of the nature and objects of the invention, reference should be made to the following detailed description, taken in connection with the accompanying drawings, in which:

FIG. 10: Co-treatment LAQ824 and Apo-2L/TRAIL induced apoptosis of HL-60/Bcl-2 cells. A. HL-60/Neo and HL-60/Bcl-2 cells were co-treated with LAQ824 and/or Apo-2L/TRAIL at the indicated doses for 24 hours. Following this, the percentage of apoptotic cells was determined by annexin-V staining and flow cytometry. Values represent mean±SE of 3 experiments. B. HL-60/Bcl-2 cells were treated with 50 nMLAQ824 and 50 μg/ml Apo-2L/TRAIL.

Following this, the cell lysates were obtained and immunoblot analyses of caspase-8, BID, tBID, PARP and XIAP were performed.

Figure 11:
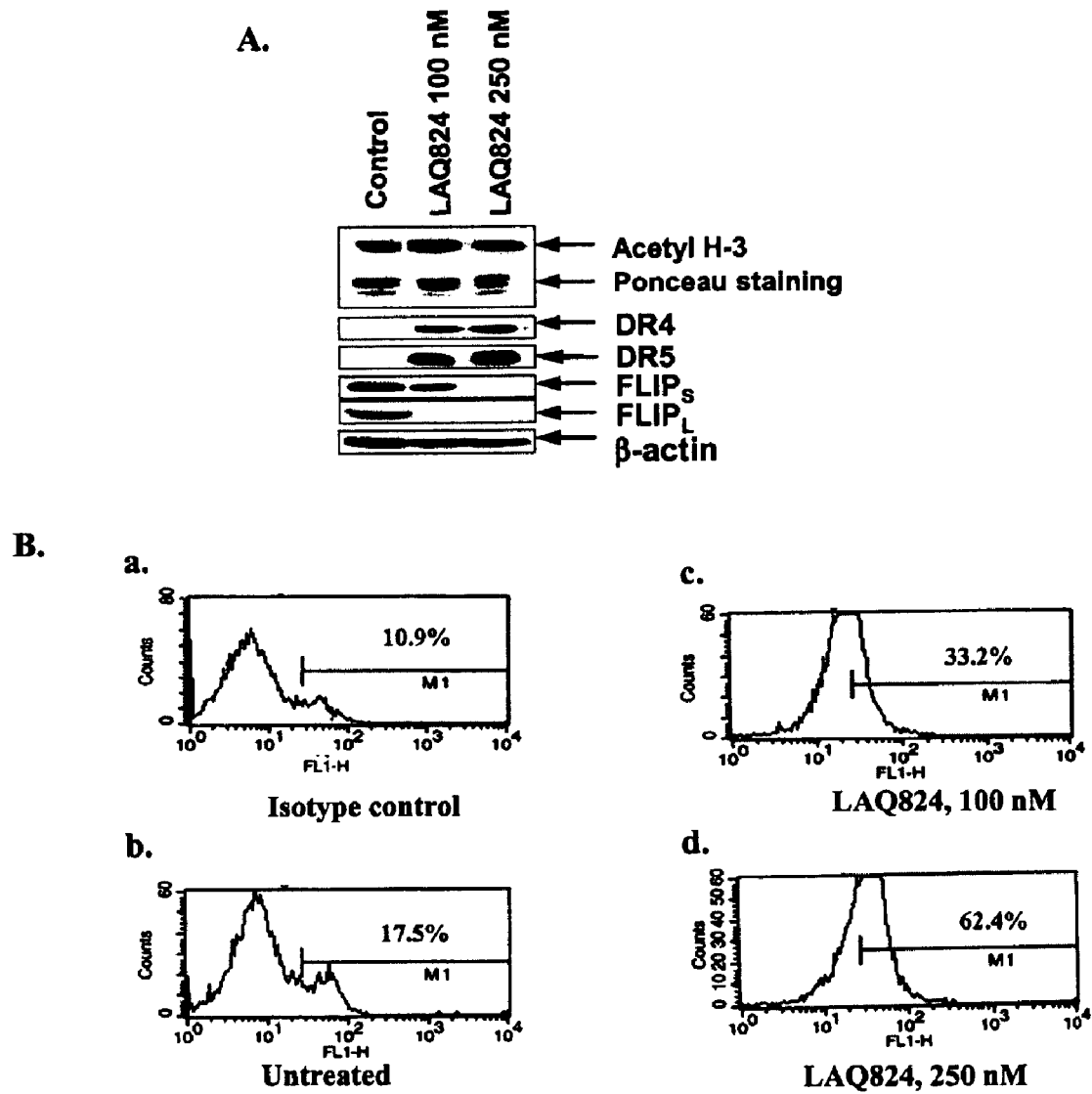

FIG. 11 LAQ824 induces histone acetylation, increases DR4 and DR5 levels, as well as down regulates $FLIP_S$ and $FLIP_L$ in primary AML cells. A. AML cells were treated with LAQ824 at the indicated concentrations for 24 hours. Following this histone protein were isolated, and the Histone H3 acetylation was detected by Western blot analysis using the anti-acetylated Histone H3 antibody. Total cell lysates of the untreated and LAQ824 treated cells were also used for immunoblot analyses of DR5, DR4, $FLIP_L$ and $FLIP_S$. β-actin was used as the loading control. B. Bone marrow mononuclear cells from a patient with AML were exposed to 100 or 250 nM of LAQ824 for 24 hours. Following this, cell-membrane expression of DR5 was determined by staining with anti-DR5 antibody and evaluated by flow cytometry. Flow cytometric histograms in panels a to d are from cells treated with: a. Isotype control, b. untreated control cells, c. 100 nM LAQ824 and d. 250 nM LAQ824.

Figure 12:
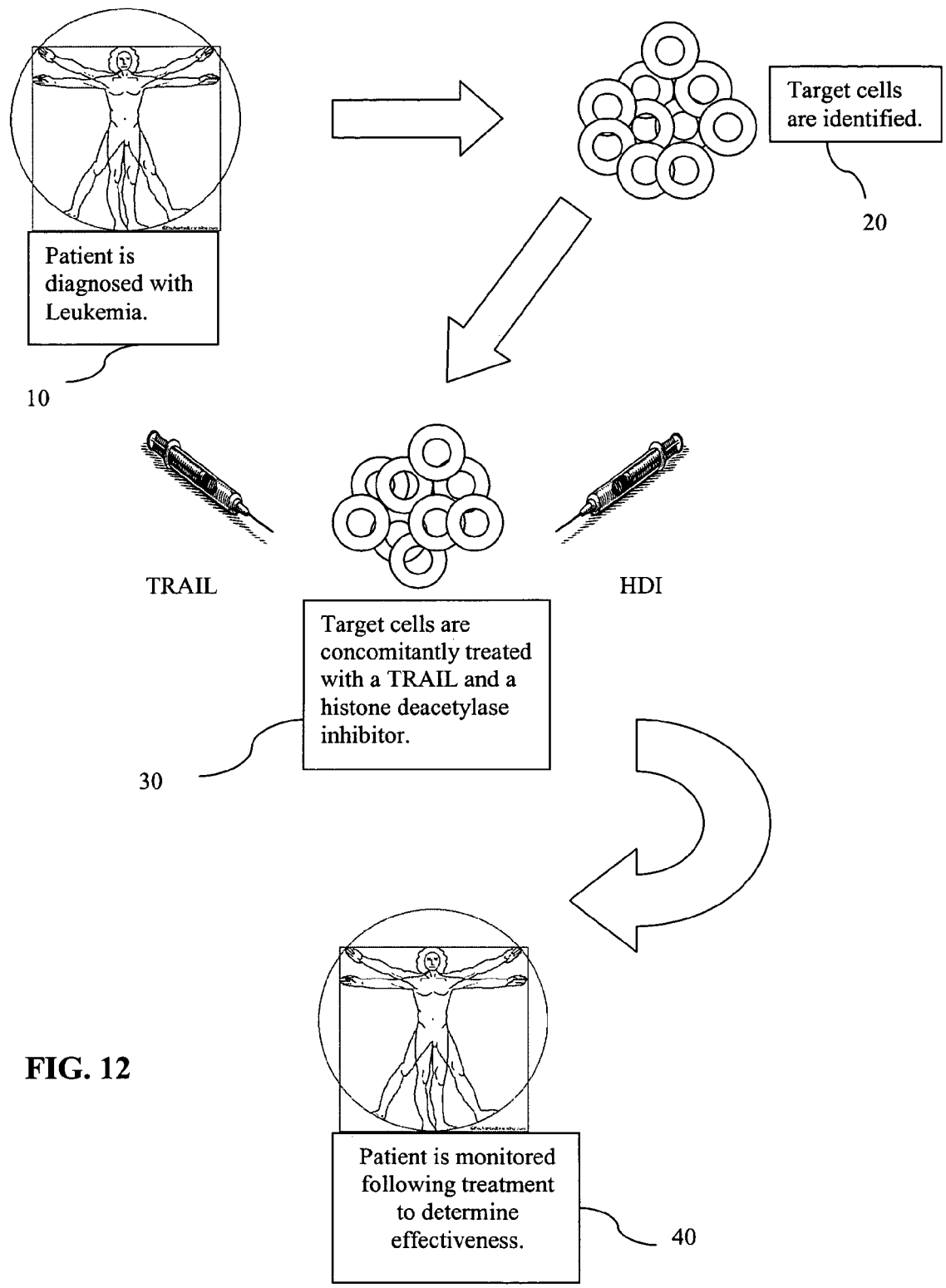

FIG. 12 is a graphic representation of the inventive method.

DETAILED DESCRIPTION OF THE PREFERRED EMBODIMENT

Treatment with the histone deacetylases (HDAC) inhibitor (HDI) LAQ824, a cinnamic acid hydroxamate, increases the acetylation of histones H3 and H4, as well as induces p21WAF1 in the human T cell acute leukemia Jurkat, B lymphoblast SKW 6.4 and AML HL-60 cells. This is associated with increased accumulation of the cells in the G1 phase of the cell cycle, as well as being accompanied by the processing and activity of caspase-9 and -3 and apoptosis. Exposure to LAQ824 increases the mRNA and protein expressions of the death receptors DR5 and/or DR4, but reduces the mRNA and protein levels of c-FLIP. As compared to treatment with Apo-2L/TRAIL or LAQ824 alone, pre-treatment with LAQ824 increases the assembly of FADD and caspase-8, but not of c-FLIP, into the Apo-2L/TRAIL-induced death inducing signaling complex (DISC). This increases the processing of caspase-8 and BID, cytosolic accumulation of the pro-death molecules cytochrome-c, Smac and Omi, as well as leading to increased activity of caspase-3 and apoptosis. Treatment with LAQ824 also down regulates the levels of Bcl-2, Bcl-$x_L$, XIAP and survivin. This is not reversed by co-treatment with either a pan-caspase or proteasome inhibitor. Partial inhibition of apoptosis exertion by Bcl-2 overexpression was reversed by co-treatment with LAQ824 and Apo-2L/TRAIL. Significantly, co-treatment with LAQ824 increases Apo-2L/TRAIL-induced apoptosis of primary AML blast samples isolated from 5 patients with AML. Taken together, these findings indicate that LAQ824 augments Apo-2L/TRAIL-induced DISC and apoptosis of human acute leukemia cells.

Experimental Method

For a list of the reagents used in the experimental method, as well as the sources of such reagents, see Table 2.

HL-60/Bcl-2 cells with ectopic overexpression of Bcl-2 and the control HL-60/Neo cells were created and maintained in culture. Primary leukemia blasts from six patients with AML in relapse were harvested from the peripheral blood or bone marrow after informed consent, as a part of a protocol study sanctioned by the local institutional review board (IRB). The purity of leukemia blasts in the samples prior to culture in LAQ824 and/or Apo-2L/TRAIL was at least 80% or more, as determined by morphologic evaluation after Wright staining.

The flow cytometric evaluation of the cell cycle status was performed and the percentage of cells in the G1, S-phase, and G2/M phases were calculated using Multicycle software (Phoenix Flow Systems, San Diego, Calif.).

After drug treatments, cells were resuspended in 100 μL of the staining solution containing annexin-V fluorescein and propidium iodide in a HEPES buffer (Annexin-V-FLUOS Staining Kit, Boehringer-Mannheim, and Indianapolis, Ind.). Following incubation at room temperature for 15 minutes, annexin V positive cells were estimated by flow cytometry, as previously described.

After drug treatment, $50 \times 10^3$ cells were washed and resuspended in PBS (pH 7.3). Cytospun preparations of the cell suspensions were fixed and stained with Wright stain. Cell morphology was determined by light microscopy. In all, five different fields were randomly selected for counting of at least 500 cells. The percentage of apoptotic cells was calculated for each experiment.

Untreated and drug-treated cells were harvested by centrifugation at 1000×g for 10 min. at 4° C. The cell pellets were washed once with ice-cold PBS and resuspended with 5 volumes of buffer (20 mM HEPES-KOH, pH 7.5, 10 mM KCl, 1.5 mM MgCl2, 1 mM sodium EDTA, 1 mM sodium EGTA, 1 mM dithiothreitol, and 0.1 mM PMSF), containing 250 mM sucrose. The cells were homogenized with a 22-gauge needle, and the homogenates were centrifuged at 10,000×g for 10 min at 4° C. The supernatants were further centrifuged at 100,000×g for 30 minutes. The resulting supernatants (S-100) were collected and the protein concentrations were determined by using the BCA protein assay reagent from Pierce Biotechnology Inc., (Rockford, Ill.). A total of 75 μg of the S-100 fraction was used for Western blot analysis of cyt c, Smac and Omi/HtrA2 (47).

Western analyses of DR4, DR5, Apo-2L, FADD, Caspase-8, c-FLIPL & S, BID, Caspase-9, Caspase-3, PARP, XIAP, cIAP1, survivin and β-actin were performed using specific antisera or monoclonal antibodies according to previously reported protocols. Horizontal scanning densitometry was performed on Western blots by using acquisition into Adobe Photo Shop (Apple, Inc., Cupertino, Calif.) and analysis by the NIH Image Program (U.S. National Institutes of Health, Bethesda, Md.). The expression of β-actin was used as a control.

Untreated or LAQ824 treated SKW6.4 or Jurkat cells were suspended at a final concentration of $10^6$ cells/ml in a pre-warmed, complete RPMI media. Cells were treated with 100 ng/ml Apo-2L/TRAIL for 2 hours at 37° C., followed by washing with 1 ml of ice-cold PBS. Cells were lysed in 500 μl lysis buffer (25 mM Tris-HCl, pH 7.2, 150 mM NaCl, 25 mM NaF, 1 mM benzamidine, 1.0% Triton X-100, 2 μg/ml aprotinin 2 μg/ml leupeptin, 1 μg/ml pepstin-A and 0.1 μg/ml PMSF) for 30 min on ice. In the untreated controls, 100 ng/ml Apo-2L/TRAIL was added after lysis of cells, to immunoprecipitate non-stimulated Apo-2L/TRAIL receptors. One-hundred micrograms of the lysates was incubated at 4° C. for 2 hours with 1 μg each of anti-Apo-2L/TRAIL receptor 1 & 2 (DR4 and DR5) antibodies, kindly provided by Immunex Corp., Seattle Wash. The immune-complexes were incubated overnight at 4° C. with 20 μl of protein A-agarose beads (Roche, Indianapolis, Ind.). The beads were recovered by centrifugation and washed twice with the lysis buffer. The pellet was resuspended in the sample buffer and analyzed by SDS-PAGE and immunoblot analysis using antibodies against caspase-8, DR5, DR4 and FADD.

Viable Jurkat cells were transfected with the cDNA of dominant negative FADD, which encodes for an 80-208 amino acid death effector domain-containing N-terminus deleted fragment (NFD-4) cloned into pcDNA 3.1 plasmid (Invitrogen Corp., Carlsbad, Calif.) or the control vector (pcDNA 3.1 Zeo), utilizing LipofectAMINE PLUS reagent (Invitrogen Corp.), as previously described. The transfectants were treated with Apo-2L/TRAIL and/or LAQ824, followed by the evaluation of the percentage of apoptotic cells.

ChIP analysis was performed by the following method. Cells were incubated overnight at a density of $0.25 \times 10^6$ cells/ml at 37° C. with 5% CO2. The next day, cells were cultured with 0, 50, 100 or 250 nM of LAQ 824 for 24 hours. Formaldehyde was then added to the cells to a final concentration of 1%, and the cells were gently shaken at room temperature for 10 minutes. Following this, the cells were pelleted, suspended in 1 ml of ice-cold PBS containing protease inhibitors (Complete, Boehringer Mannheim). Cells were again pelleted, resuspended in 0.5 ml of SDS lysis buffer (1% SDS/1.0 mM EDTA/50 mM Tris-HCl, pH 8.1), and incubated on ice for 20 minutes. Lysates were sonicated with 15-sec bursts. Debris was removed from samples by centrifugation for 20 min at 15,000×g at 4° C. An aliquot of the chromatin preparation (100 µl) was set aside and designated as Input Fraction. The supernatants were diluted 3-fold in the immunoprecipitation buffer (0.01% SDS/1.0% Triton X-100/1.2 mM EDTA/16.7 mM Tris-HCl, pH 8.1/150 mM NaCl), and 80 µL of 50% protein A sepharose slurry containing 20 µg sonicated salmon sperm DNA and 1 mg/ml BSA in the TE buffer (10 mM Tris-HCl, pH 8.0/1 mM EDTA) was added and incubated by rocking for 2 hours at 4° C. Beads were pelleted by centrifugation, and supernatants were placed in fresh tubes with 5 µg of the anti-acetylated histone H3 antibody, anti-acetylated histone H4 antibody, or normal rabbit serum and incubated overnight at 4° C. Protein A sepharose slurry (60 µL) was added, and the samples were rocked for 1 hour at 4° C. Protein A complexes were centrifuged and washed 3 times for 5 minutes each with immunoprecipitation buffer and 2 times for 5 minutes each with immunoprecipitation buffer containing 500 mM NaCl. Immune complexes were eluted twice with 250 µl of elution buffer (1% SDS/0.1 M NaHCO3) for 15 minutes at room temperature. Twenty microliters of 5 M NaCl was added to the combined eluates, and the samples were incubated at 65° C. for 24 h. EDTA, Tris-HCl, pH 6.5, and proteinase K were then added to the samples at a final concentration of 10 mM, 40 mM, and 0.04 µg/µl, respectively. The samples were incubated at 37° C. for 30 minutes. Immunoprecipitated DNA (both immunoprecipitation samples and Input) was recovered by phenol/chloroform extraction and ethanol precipitation and analyzed by PCR. DR5 and p21WAF1-specific primers were used to perform PCR on DNA isolated from ChIP experiments and Input samples. The optimal reaction conditions for PCR were determined for each primer pair. For DR5 promoter PCR: forward primer was 5'-GGA GGA AAG AGA AAG AGA GAA AGG AAG G-3' and reverse primer was 5'-TTG GGG GAA ATG AGT TGA GGG AGG-3'. The PCR reaction contained 0.2 mM concentration of dATP, dCTP, dGTP and dTTP, 200 nM of each DR5 promoter primer, 1.5 mM of Mgcl2, and 10× PCR buffer containing Tris-HCL (ph 8.0) 500 mM KCL, and 1 U of Tag polymerase (Invitrogen Carlsbad, Calif.). The primer pairs used for p21WAF1 analysis were: 5'-GGT GTC TAG GTG CTC CAG GT-3' (dp1), 5'-TGTCTAGGTGCTCCAG-3' (up1). The reactions were performed at 95° C. for 5 minutes, and were followed by 35 cycles of denaturating at 95° C. for 1 minute, annealing at 56° C. for 1 minute and extension at 72° C. for 1 minute. The PCR products were separated on 2% agarose/eithidium bromide gel. The size of the amplified product was 253 base pairs. The ratio between the immunoprecipitated DNA and Input DNA was calculated for each treatment and primer set. The fold increases after treatment with LAQ824 was calculated from the indicated ratio.

A RiboQuant Multi-Probe RNase Protection Assay System was used according to the manufacturer's instructions (BD/PharMingen, San Diego, Calif.), and as previously described. A probe set, hAPO-3d (FLICE, FAS, DR5, DR4, and TRAIL) was used for T7 RNA-polymerase directed synthesis of [α-32P] UTP-labeled antisense RNA probes. The probe set contains the DNA templates, including Glyceraldehyde-3-phosphate dehydrogenase (GAPDH) used as internal control. The probes ($1 \times 10^6$ cpm/reaction) were hybridized with 20 µg of RNA isolated from the SKW 6.4 and Jurkat leukemia cells, following treatment with 100 nM LAQ824 at different time points using the RNeasy Mini kit (Qiagen, Valencia, Calif.). After overnight hybridization, samples were digested with RNase to remove single-stranded (non-hybridized) RNA. The remaining probes were resolved on 5% denaturing polyacrylamide gel and analyzed by autoradiography.

Total RNA was isolated from cells utilizing a TRIZOL LS reagent (Invitrogen Carlsbad, Calif.). RT-PCR analysis was performed, as previously described. The RNA (1.0 µg) was reverse-transcribed into cDNA by using SuperScript II RT (Invitrogen Carlsbad, Calif.) according to the manufacturer's protocol. For the c-FLIP PCR, the primer sequences were as follows: forward primer: 5'-GCC CGA GCA CCG AGA CTA CG-3'; reverse primer: 5'-AGG GAC GGD GAG CTG TGA GAC TG-3'. β-actin forward primer: 5'-CTA CAA TGA GCT GCG TGT GG-3', and reverse primer: AAG GAA GGC TGG AAG AGT GC. The PCR reaction containing 0.2 mM concentration of dATP, dCTP, dGTP, dTTP, 200 nM concentration of each c-FLIP primers and 50 nM of each β-actin primers, 1.5 mM of MgCl2, and 10× PCR buffer containing Tris-HCL (pH 8.0), 500 mM KCL and 1 U of Tag polymerase (Invitrogen Carlsbad, Calif.). The reaction was performed at 95° C. for 5 min, and was followed by 30 cycles of denaturating at 95° C. for 45 seconds, annealing at 52° C. for 45 seconds and the extension at 72° C. for one minute. The PCR products were separated on a 2% agarose/eithidium bromide gel. The size of the amplified products was 395 bases pairs for the c-FLIP and 527 base pairs for β-actin product, respectively Data were expressed as mean±SEM. Comparisons used student's t test or ANOVA, as appropriate. P values of <0.05 were assigned significance.

Findings

Figure 1:
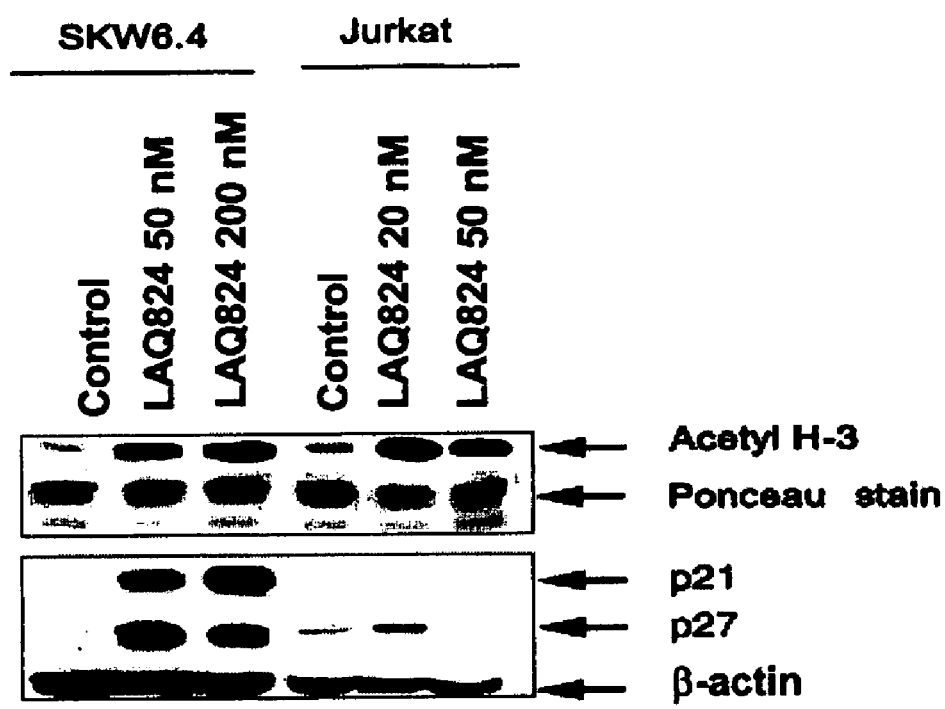
FIG. 1 LAQ824 induces histone acetylation and levels of p21 and p27. SKW6.4 and Jurkat cell were treated with LAQ824 at the indicated concentrations for 24 hours. Following the isolation of histones, Ac-histone H3 acetylation was detected by Western blot analysis using the anti-acetylated Ac-histone H3 antibody. Total cell lysates were also probed with anti-p21 and anti-p27 antibodies. β-actin levels served as the control for protein loading.
Figure 2:
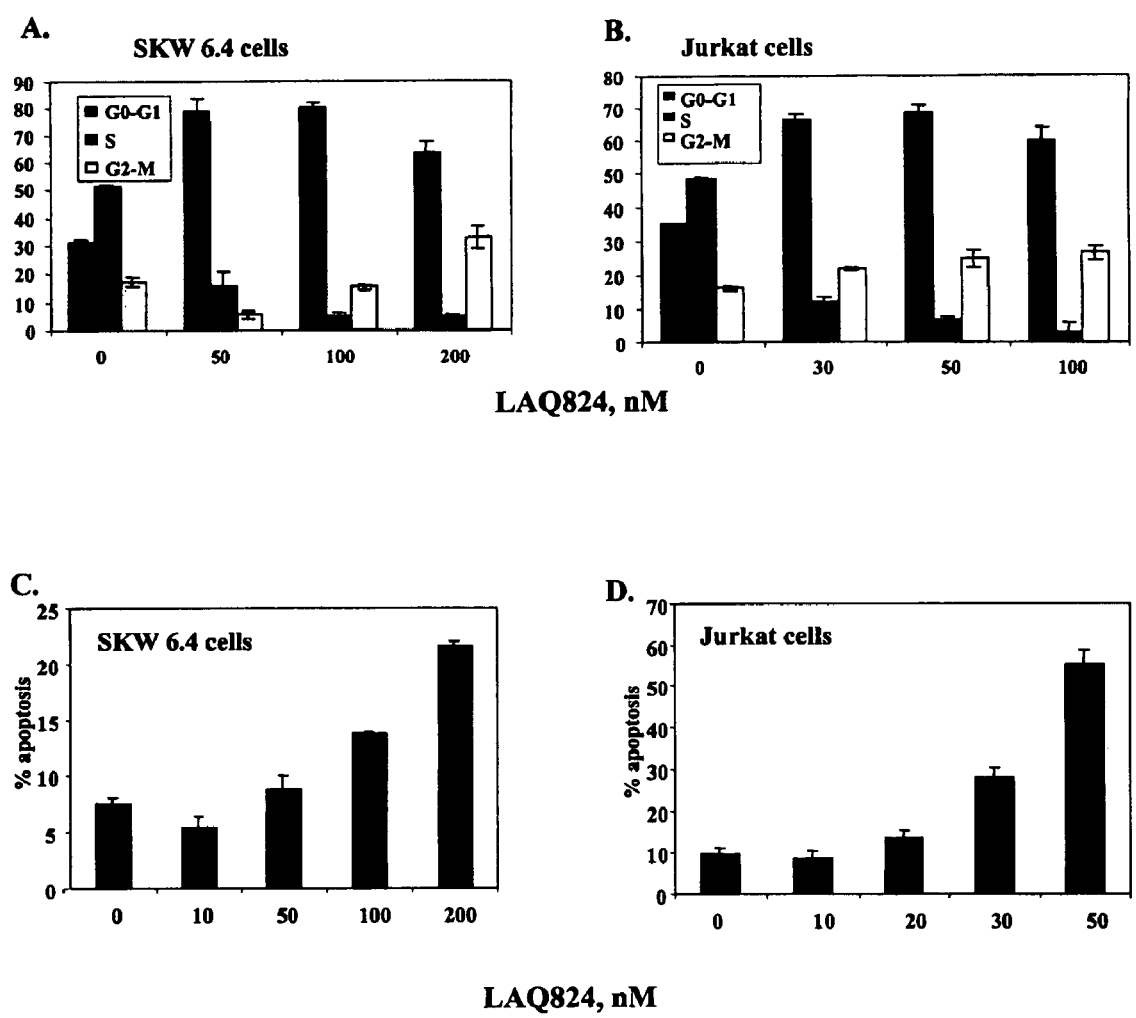
FIG. 2 LAQ824 induces accumulation in the G1 phase of the cell cycle and apoptosis. SKW 6.4 (A) and Jurkat (B) cells were treated with the indicated concentration of LAQ824 for 24 hours. Following this, the cell cycle status and the percentage of apoptotic cells were determined by flow cytometry. Values represent mean±SE of 3 experiments.

LAQ824 Treatment Induces p21 and p27, as Well as Causes Cell Cycle G1 Phase Accumulation and Apoptosis of Jurkat and SKW6.4 Cells It has previously been reported that treatment with LAQ824 (5 to 250 nM) inhibits the in vitro HDAC activity in a dose dependent manner in the HeLa cell nuclear extracts. Therefore, the effect of LAQ824 on histone acetylation, p21 and p27 levels, as well as on growth arrest and apoptosis of human acute leukemia Jurkat and SKW 6.4 cells was determined. Treatment with 50 or 200 nM LAQ824 for 24 hours increased the acetylation of histone H3 (FIG. 1) and histone H4 (data not shown) in Jurkat and SKW 6.4 cells. LAQ824 mediated histone hyperacetylation was associated with a dose-dependent increase in the levels of p21 in SKW 6.4 but not Jurkat cells (FIG. 1). In contrast, although exposure to 50 nM LAQ824 increased the intracellular levels of p27 in both SKW 6.4 and Jurkat cells, treatment with 200 nM of LAQ284 attenuated the p27 levels in both cell-types (FIG. 1). These results are consistent with the previous reports that LAQ824 induces the hyperacetylation of nucleosomal histones associated with p21 but not p27 gene promoter, thereby transitionally upregulating p21 but increasing p27 levels by alternative non-transcriptional mechanism. The effect of LAQ824 on the cell cycle status of SKW 6.4 and Jurkat cells is shown in FIGS. 1A and 1B, respectively. The results show that exposure to LAQ824 for 24 hours markedly increased the percentage of cells in the G1 phase and a decline in the S phase of the cell cycle. Similar effects were observed in the AML HL-60 cells (data not shown). Importantly, exposure to 10 to 200 nM of LAQ824 for 24 hours induced apoptosis in a dose dependent manner, more in Jurkat (FIG. 1D) than in SKW 6.4 cells, as detected by positive staining for annexin V (FIG. 1D). Although not shown, treatment with 100 or 200 nM LAQ824 induced apoptosis in more than 90% of Jurkat cells. These finding with respect to LAQ824 induced apoptosis were also confirmed by the morphologic assessment of apoptosis (data not shown).

Figure 3:
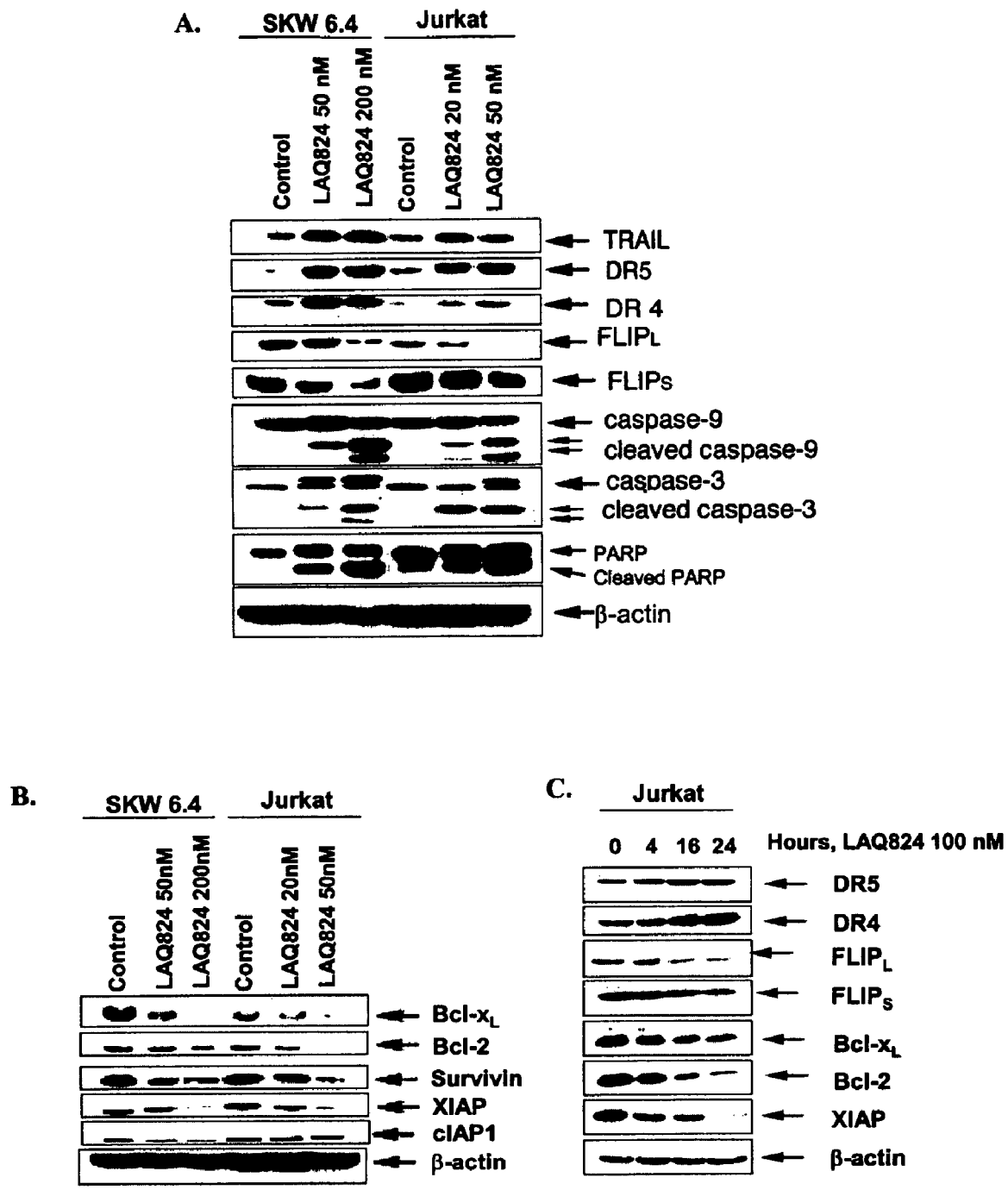
FIG. 3 LAQ824 treatment increases Apo-2L/TRAIL, DR4 and DR5 expression but downregulates XIAP, survivin, Bcl-2, and Bcl-$x_L$ expression in SKW 6.4 and Jurkat cells. Cells were treated with LAQ824 at the indicated concentrations for 24 hours. Following this, the cell-lysates were obtained. A. Immunoblot analyses of Apo-2L/TRAIL, DR5, DR4, $FLIP_L$, FLIPs, as well as caspase-8, -9 and -3 and their cleaved fragments. B. Immunoblot analyses of Bcl-$x_L$, survivin, XIAP, cIAP-1 and Bcl-2. β-actin levels served as the loading control. C. Alternatively, cells were treated with 100 nM LAQ824 for 4, 16 or 24 hours and cell lysates were analyzed by immunoblot analyses of DR4, DR5, c-$FLIP_L$, c-FLIPs, XIAP, Bcl-2 and Bcl-$x_L$. β-actin levels served as the loading control.
Figure 4:
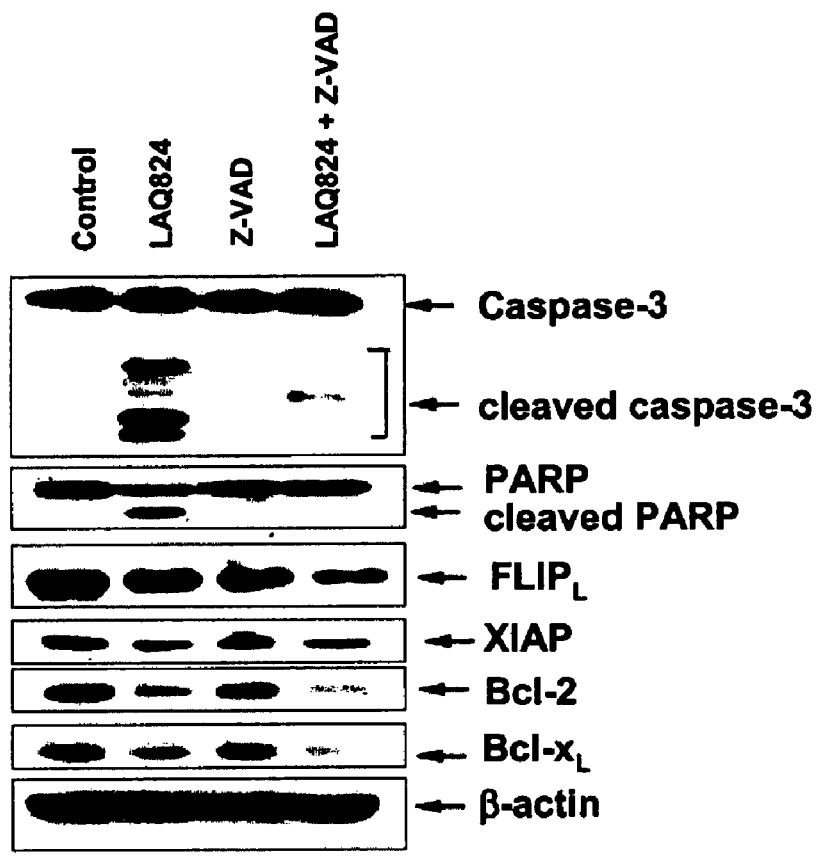
FIG. 4 LAQ824 mediated attenuation of Bcl-2, Bcl-$x_L$, XIAP or $cFLIP_L$ is neither dependent on caspase activity nor enhanced by proteasomal degradation. A. Jurkat cells were treated with 50 nM LAQ824 and/or 50 μM zVAD-fmk for 24 hours, and cell lysates were obtained. Immunoblot analyses of PARP, caspase-3, Bcl-2, Bcl-$x_L$, XIAP and c-$FLIP_L$ were performed on the lysates. β-actin levels served as the loading control. B. Jurkat cells were treated with 100 nM LAQ824 and/or 10 μM ALLnL for 24 hours and cell lysates were obtained. Immunoblot analyses of PARP, caspase-3, Bcl-2, Bcl-$x_L$, XIAP and $cFLIP_L$ were performed on the lysates. β-actin levels served as the loading control.
Figure 4:
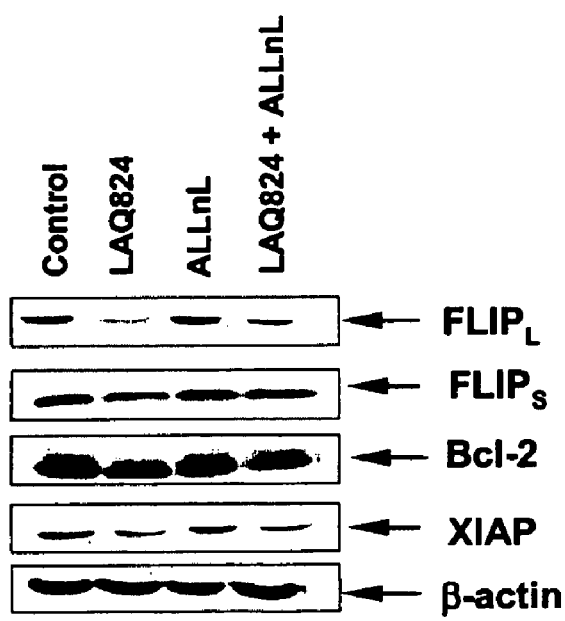
Figure 5:
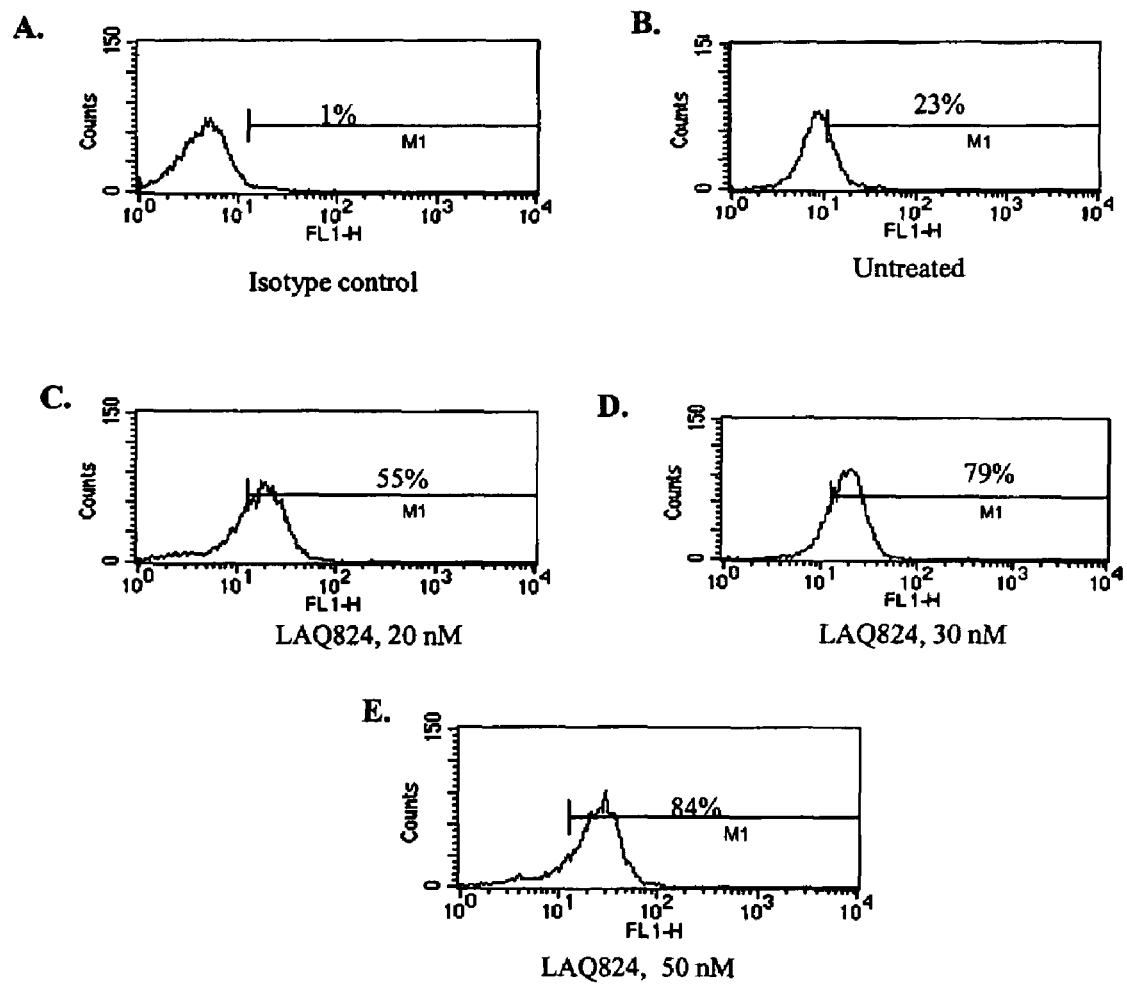
FIG. 5 Treatment with LAQ824 increases DR5 expression on the cell membrane. Jurkat cells were exposed to 20, 30 or 50 nM of LAQ824 for 24 hours. Following this, the cell membrane expression of DR5 was determined in untreated or LAQ824 treated cells by staining with anti-DR5 antibody followed by flow cytometry. The histograms in panels A to E are representative of 3 experiments and derived from cells treated as follows: A. isotype control, B. untreated control cells, C. LAQ824, 20 nm, D. LAQ824, 30 nM, and E. LAQ824, 50 nM. Values in each panel represent the % of cells showing positive staining.

LAQ824 Induces DR4, DR5 and Apo-2L/TRAIL Bur Attenuates the Levels of FLIP, Bcl-2 and IAP Family of Proteins The effect of LAQ824 on the intracellular levels of the molecular determinants of the extrinsic and intrinsic pathway of apoptosis in SKW 6.4 and Jurkat cells was determined based on its ability to induce apoptosis. FIG. 3A shows that exposure to LAQ824 for 24 hours induced Apo-2L/TRAIL, DR4 and DR5 levels. However, LAQ824 treatment did not affect the expression of the decoy receptors for Apo-2L/TRAIL, DcR1 and DcR2 (data not shown). In contrast, treatment with LAQ824 attenuated the levels of FLIPL and FLIPS in both SKW 6.4 and Jurkat cells (FIG. 3A). This was associated with the processing of caspase-9 & -3, suggesting that treatment with LAQ824 not only induces the intrinsic pathway but also primes the cells to the extrinsic pathway induced by Apo-2L/TRAIL. In addition, treatment with LAQ824 also attenuated the levels of Bcl-$x_L$, Bcl-2, XIAP, c-LAP and survivin (FIG. 3B), which may collectively further lower the threshold to apoptosis due to Apo-2L/TRAIL. FIG. 3C shows that in Jurkat cells, these effects of were evident following exposure intervals to LAQ824 of 16 hours or less. Similar observations were made when SKW 6.4 cell were exposed to 200 nM LAQ824 (data not shown). Since previous reports have suggested that during apoptosis, several of the determinants of apoptosis belonging to the Bcl-2 and IAP family may be processed by caspases and/or degraded by the proteasome. FIG. 4A demonstrates that in Jurkat cells co-treatment with z-VAD-fmk, which inhibited the processing of caspase-3 and PARP, was unable to reverse the attenuating effect of LAQ824 on XIAP, Bcl-2, Bcl-$x_L$ and c-FLIPL. In addition, co-treatment with the proteasomal inhibitor ALLnL did not restore the levels of XIAP, Bcl-2, c-FLIPL and c-FLIPS attenuated by LAQ824 (FIG. 4B). Similar observations were also made in SKW 6.4 cells co-treated with LAQ824 and z-VAD-fmk or ALLnL (data not shown). Next, we determined, whether LAQ824 treatment increases the cell surface expression of DR5, DR4 and Apo-2L/TRAIL. FIG. 5 demonstrates that treatment of Jurkat cells with LAQ824 induced the cell-membrane expression of DR5, as determined by flow cytometry. However, LAQ824 treatment only slightly increased DR4 levels, and Apo-2L/TRAIL expression was not increased in Jurkat or SKW 6.4 cells (data not shown).

Figure 6:
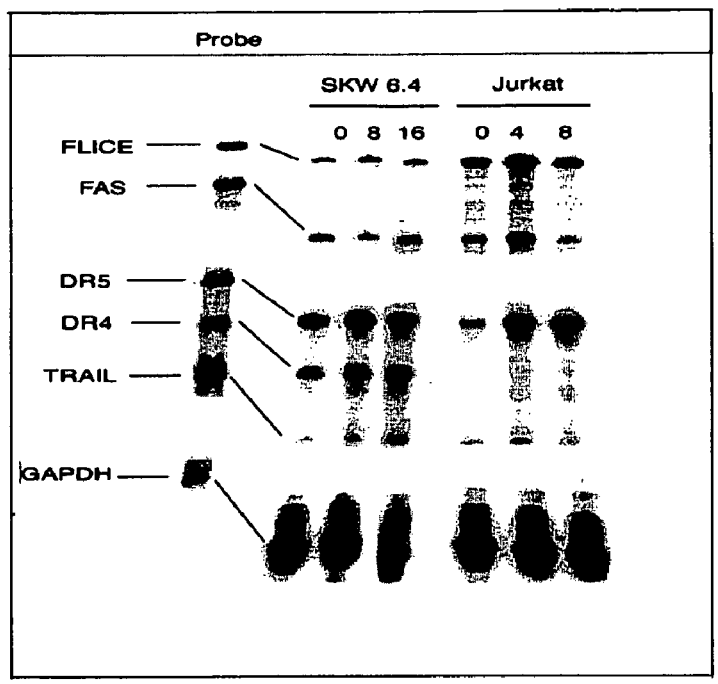
FIG. 6 Treatment with LAQ824 increases the mRNA expression of DR4 and DR5, and increases the association of the DR5 gene with the acetylated histone H3 and H4 in chromatin. A. After exposure of SKW 6.4 and Jurkat cells to 100 nM LAQ824 for the indicated time intervals (hours), mRNA expression levels of the indicated genes were determined using a Riboquant Multi-Probe RNase Protection Assay. B. Soluble chromatin was immunoprecipitated with anti-acetylated histone H3 and H4 antibodies. PCR primers for the DR5 promoter were used to amplify the DNA isolated from the immunoprecipitates. PCR products were scanned and quantified. The lanes represent culture conditions for 4 hours for input cell lysate (lanes 6, 7 and 8) and immunoprecipitated chromatin (lanes 3, 4 and 5) as follows: lane 3 and 6, untreated SKW 6.4 cells; lanes 4 and 7, SKW 6.4 cells treated with 100 nM LAQ824; lanes 5 and 8, and SKW6.4 cells treated with 200 nM LAQ824; lane 1 is the negative control for PCR product and lane 2, unrelated antibody control. C. The ratio between input DNA and precipitated DNA was calculated for each treatment. The fold-increase after LAQ824 treatment was calculated and is shown in the table.
Figure 6:
Figure 7:
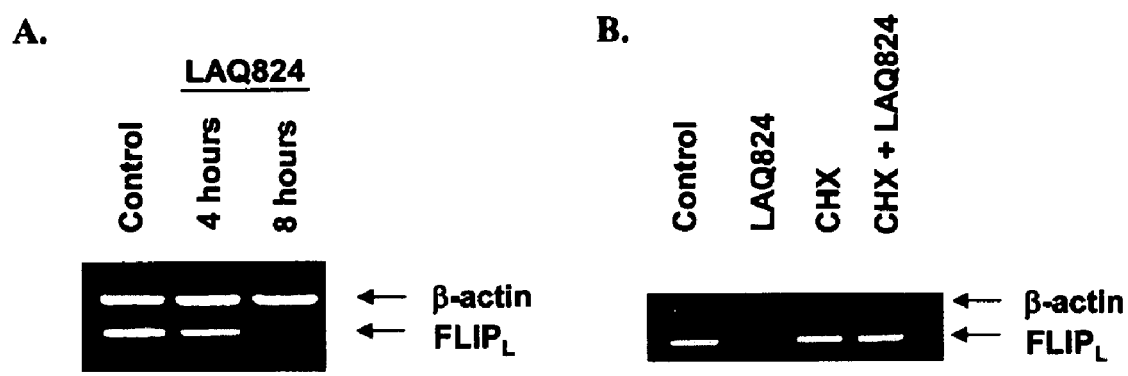
FIG. 7 Treatment with LAQ824 decreases the mRNA expression of c-$FLIP_L$, which is reversed by the co-treatment with cycloheximide. Following treatment of Jurkat cells with 50 nM of LAQ824 for 4 or 8 hours mRNA levels of cFLIP were determined by RT-PCR with β actin mRNA as the control. C. Following treatment of Jurkat cells with 50 nM of LAQ824 and/or 10 μg/ml of cycloheximide for 8 hours, mRNA levels of cFLIP and β actin were determined by RT-PCR, and are represented, as follows: lane 1, untreated cells; lane 2, LAQ824 treatment; lane 3, cycloheximide treatment; and lane 4, combined treatment with LAQ824 and cycloheximide.

LAQ824 Increase the mRNA Levels of DR4 and DR5 But Depletes the mRNA of c-FLIPL Next, the effect of LAQ824 on the mRNA levels of c-FLIPL, DR5, DR4 and Apo-2L/TRAI, utilizing a multi-probe RNAse protection assay and estimated by densitometry with GAPDH mRNA as the loading control was determined. FIG. 6A demonstrates that treatment with LAQ824 for 8 or 16 hours increased the mRNA expression of DR5 (2.4 fold) and FAS (1.5 fold). DR4 levels increased by 2.2 fold only in SKW 6.4 cells. Exposure to LAQ824 only minimally affected the mRNA levels of Apo-2L/TRAIL and caspase-8 (FLICE). It remained to be determined whether the promoter of DR5 is associated with acetylated histones, which would explain why LAQ824 would transcriptionally upregulate DR5 mRNA levels, by causing histone hyperacetylation. The results of the chromatin immunoprecipitation (ChIP) analyses performed on the lysates of the untreated or LAQ824 treated Jurkat cells showed that treatment with 100 and 200 nM LAQ824 for 8 hours increased the level of the DR5 promoter associated with acetylated histones H3 and H4 by 3.3 and 5.7 fold, respectively (mean of three experiments) (FIGS. 6B & C). Similar results were also obtained in LAQ824 treated SKW 6.4 cells (data not shown). As has been previously reported, LAQ824 also increased the association of p21WAF1 promoter DNA with acetylated histones in Jurkat and SKW 6.4 cells (data not shown). In contrast to the increase in the DR5 and DR4 mRNA levels, exposure to LAQ824 for eight hours inhibited the mRNA level of c-FLIP$_L$ by 75%, as determined by an RT-PCR assay (FIG. 7A). This was reversed by co-treatment with LAQ824 and cyclohiximide (CHX) (FIG. 7B). These results indicate that LAQ824 mediated repression of the c-FLIP$_L$ message required new protein synthesis. These results also support the interpretation that LAQ824 augments the levels and activity of a transcriptional repressor for c-FLIP$_L$, an outcome that is neutralized by co-treatment with CHX.

Figure 8:
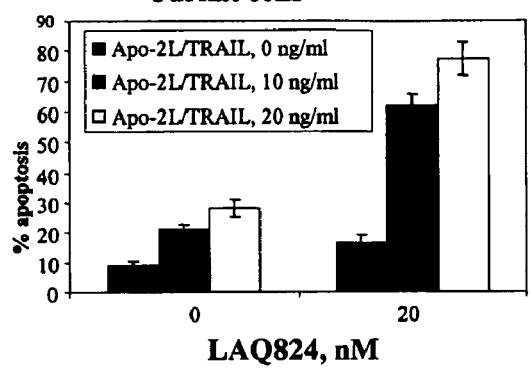
FIG. 8 Treatment with LAQ824 enhances Apo-2L/TRAIL induced DISC assembly, DISC activity and apoptosis. A. Jurkat and B. SKW 6.4 cells were treated with LAQ824 and/or Apo-2L/TRAIL at the indicated doses for 24 hours. Following this, the percentage of apoptotic cells was determined by annexin-V staining followed by flow cytometry. Values represent mean ±SE of 3 experiments. C. Following treatment of Jurkat cells with LAQ824 (20 nM) and/or Apo-2L/TRAIL (10 ng/ml) for 24 hours, either the total cell lysates were utilized for immunoblot analyses of caspase-8, BID, caspase-3 and PARP, or the cytosolic (S100) fractions of cells were either used for immunoblot analysis of cytochrome (cyt) c, Omi or Smac (D), β-Actin expression was used as the loading control. E. SKW 6.4 cells were treated with 100 nM LAQ824 for 24 hours or 100 ng/ml Apo-2L/TRAIL for 2 hours, or LAQ824 followed by Apo-2L/TRAIL. Following these treatments, cell lysates were immunoprecipitated with anti-DR5 antibody and immunoblotted with anti-caspase-8, -FADD and anti-cFLIP antibody and F. Jurkat cells were transfected with the cDNA of dominant negative FADD, and the transfectants were treated with Apo-2L/TRAIL and/or LAQ824 for 24 hours. Following this the percentage of apoptotic cells were estimated by morphologic evaluation through light microscopy.
Figure 8:
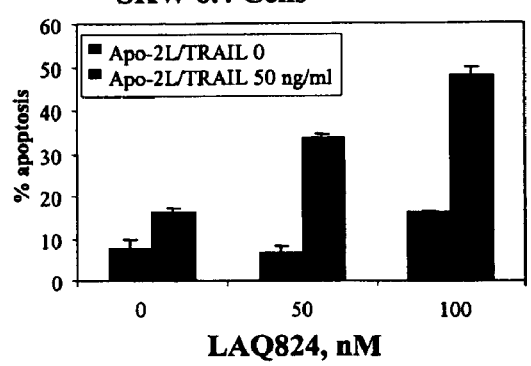
Figure 8:
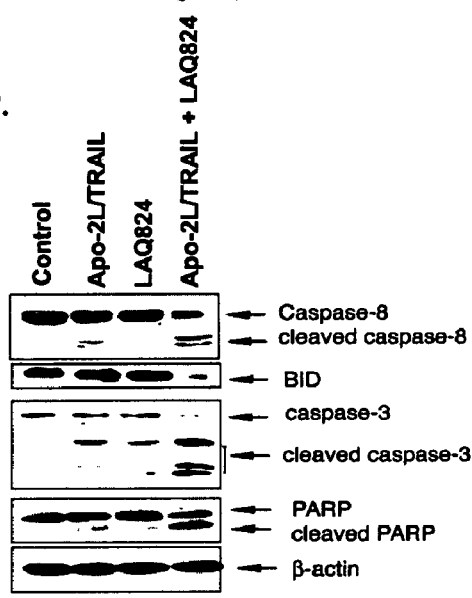
Figure 8:
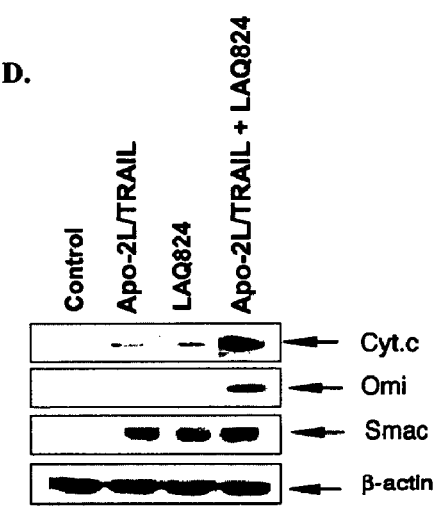
Figure 8:
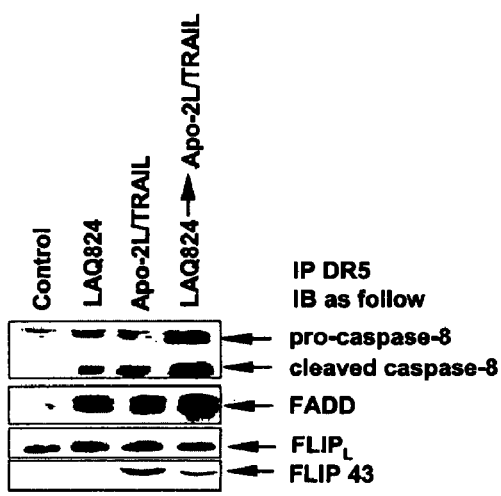
Figure 8:
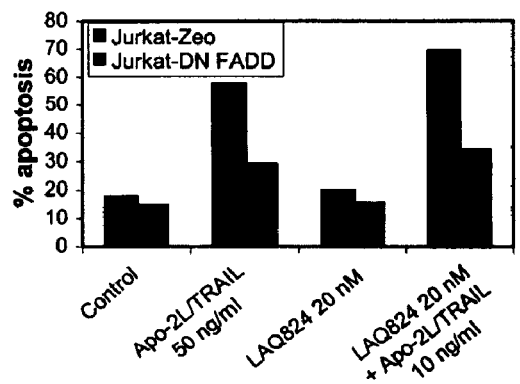

LAQ824 Enhances Apo-2L/TRAIL-Induced DISC Assembly and Activity and Apoptosis Next to be determined were the effects of LAQ824 on Apo-2L/TRAIL-induced DISC and apoptosis, since agents that lower c-FLIP levels and increase DR5 and DR4 levels have been previously shown to enhance Apo-2L/TRAIL-induced DISC activity and apoptosis of leukemia and epithelial cancer cells. FIGS. 8A & B demonstrate that co-treatment with LAQ824 and Apo-2L/TRAIL induced significantly more apoptosis of Jurkat and SKW 6.4 cells, as compared to treatment with either agent alone ($p \leq 0.05$). Concomitantly, combined treatment with LAQ824 (20 nM) and Apo-2L/TRAIL (10 ng/ml) for 24 hours, versus treatment with LAQ824 or Apo-2L/TRAIL alone, induced greater processing of caspase-8 and BID, as well as increased processing and the PARP cleavage activity of caspase-3 (FIG. 8C). This involved increased mitochondrial permeability transition, since co-treatment with LAQ824 and Apo-2L/TRAIL, versus LAQ824 or Apo-2L/TRAIL alone, also caused more accumulation of the pro-death molecules cytochrome c, Smac and Omi into the cytosol (FIG. 8D). To determine the effect of treatment with LAQ824 on Apo-2L/TRAIL-induced DISC, the recruitment of caspase-8, FADD and c-FLIPL into the immunoprecipitates of DR5 and DR4 following treatment with Apo-2L/TRAIL (100 nM for two hours) versus treatment with LAQ824 (100 nM for 24 hours) followed by Apo-2L/TRAIL were compared. As shown in FIG. 8E, pre-treatment with LAQ824 induced more recruitment of FADD and caspase-8 but not c-FLIPL into the immunoprecipitates of DR4 & DR5, resulting in greater processing of caspase-8 but less of c-FLIPL. It was not possible to detect any recruitment of c-FLIPS to Apo-2L/TRAIL-induced DISC in cells pre-treated with LAQ824 (data not shown). To determine whether the increased assembly and activity of DISC due to upregulation of DR4 and DR5 and down regulation of c-FLIPL and c-FLIPS contributed to enhancement of Apo-2L/TRAIL-induced apoptosis, the inventor determined the effect of the transient transfection of the DED-depleted cDNA of DN-FADD on apoptosis of Jurkat cells induced by Apo-2L/TRAIL or co-treatment with LAQ824 and Apo-2L/TRAIL. As compared to Jurkat cells transfected with the control vector alone (Jurkat-Zeo cells), apoptosis induced by treatment with Apo-2L/TRAIL or by co-treatment with LAQ824 and Apo-2L/TRAIL was inhibited in Jurkat cells transfected with DN-FADD (FIG. 8F). Importantly, the sensitizing effect of LAQ824 on Apo-2L/TRAIL-induced apoptosis was reduced in Jurkat-DN FADD versus Jurkat-Zeo cells (FIG. 8F). These findings suggest that LAQ824-induced modulations of the components and activity of Apo-2L/TRAIL-induced DISC contribute toward the overall potentiating effect of LAQ824 on Apo-2L/TRAIL-induced apoptosis.

Figure 9:
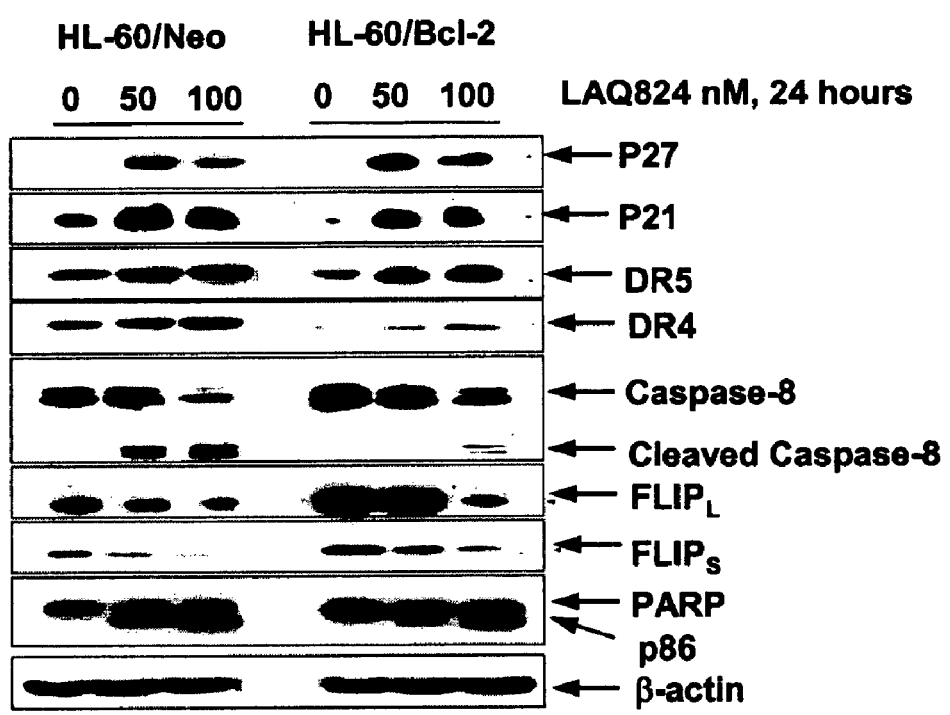
FIG. 9 LAQ824 increases p21, p27, DR4 and DR5, down regulates FLIPs and $FLIP_L$, as well as causes the processing of caspase-8 and PARP in HL-60 cells with overexpression of Bcl-2. HL-60/Neo and HL-60/Bcl-2 cells were treated with 50 or 100 nM of LAQ824 for 24 hours. Following this, cell-lysates were obtained, and immunoblot analyses of p21, p27, DR4, DR5, caspase-8, PARP, $FLIP_L$ and FLIPs were performed. B-actin levels served as the loading control.
Figure 10:
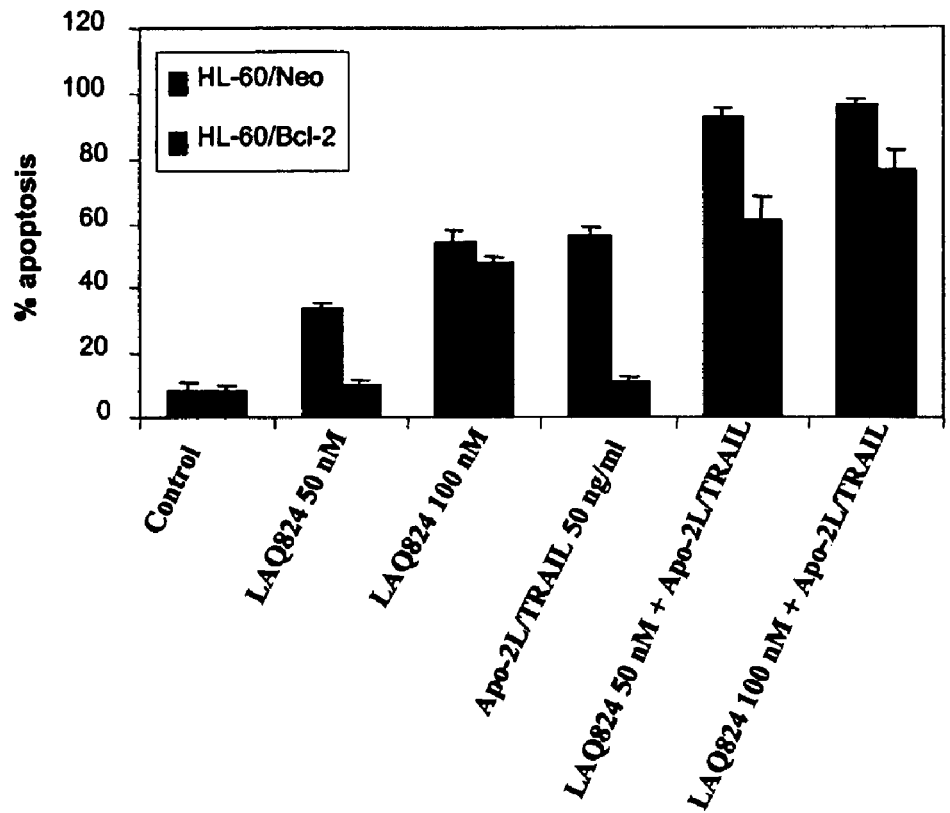
FIG. 10 Co-treatment LAQ824 and Apo-2L/TRAIL induced apoptosis of HL-60/Bcl-2 cells. A. HL-60/Neo and HL-60/Bcl-2 cells were co-treated with LAQ824 and/or Apo-2L/TRAIL at the indicated doses for 24 hours. Following this, the percentage of apoptotic cells was determined by annexin-V staining and flow cytometry. Values represent mean±SE of 3 experiments. B. HL-60/Bcl-2 cells were treated with 50 nMLAQ824 and 50 μg/ml Apo-2L/TRAIL. Following this, the cell lysates were obtained and immunoblot analyses of caspase-8, BID, tBID, PARP and XIAP were performed.
Figure 10:
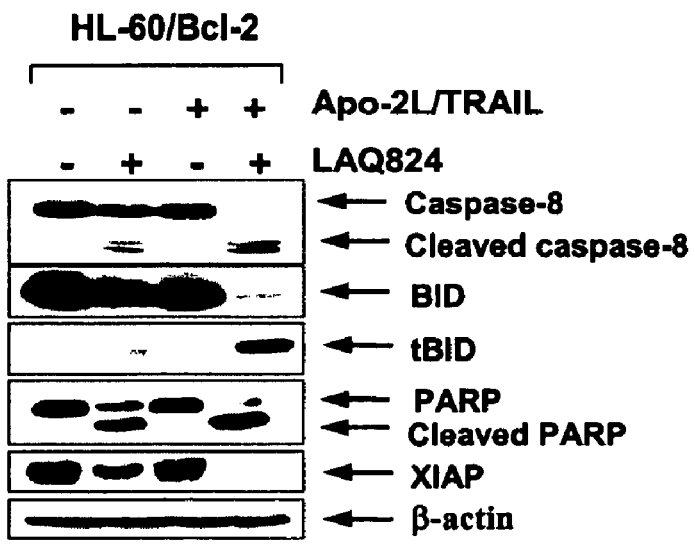

Combined Treatment with LAQ824 and Apo-2L/TRAIL Overcomes the Inhibition of Apoptosis by Bcl-2 Overexpression The effects of LAQ824 and/or Apo-2L/TRAIL were compared in HL-60/Bcl-2 cells that possess ectopic overexpression of Bcl-2 (5-fold) versus the control HL-60/Neo cells. FIG. 9 demonstrates that LAQ824 mediated increase in p21, p27, DR4 & 5 levels, as well as decline in FLIPL and FLIPS levels were approximately similar, as compared to the untreated in HL-60/Bcl-2 versus HL-60/Neo cells. As has been previously reported, Apo-2L/TRAIL-induced apoptosis was inhibited in HL-60/Bcl-2 versus HL-60/Neo cells (FIG. 10A). Although following treatment with 50 nM LAQ824 the PARP-cleavage activity of caspase-3 and processing of caspase-8 was also inhibited in HL-60/Bcl-2 cells, exposure to higher level of LAQ824 (100 nM) resulted in similar processing of PARP and caspase-8 in HL-60/Bcl-2 and HL-60/Neo cells (FIG. 9). Additionally, co-treatment with 50 ng/ml of Apo-2L/TRAIL and LAQ824 (50 or 100 nM) induced more apoptosis than either agent alone in HL-60/Bcl-2 cells, consistently in over 50% of HL-60/Bcl-2 cells (FIG. 10A). This was associated with more processing of caspase-8 and BID, with the generation of higher levels of tBID (FIG. 10B). It was also associated increased PARP cleavage activity of caspase-3 and down regulation of XIAP (FIG. 10B). These findings suggests that the inhibition of apoptosis due to Apo-2L/TRAIL and lower levels of LAQ824 by Bcl-2 can be overcome by treatment with higher levels of LAQ824 or co-treatment with Apo-2L/TRAIL and LAQ824.

Co-Treatment with LAQ824 Overcomes Resistance to Apo-2L/TRAIL-Induced Apoptosis of Leukemia Blasts From Patients with AML in Relapse The sensitivity of fresh AML cells procured from patients with relapsed AML to Apo-2L/TRAIL and/or LAQ824-induced apoptosis was next to be determined. Table 1 shows that all six samples of AML blasts were resistant to apoptosis induced by Apo-2L/TRAIL (100 ng/ml). In contrast, exposure to LAQ824 (100 nM) induced more apoptosis of the primary AML cells. In every sample evaluated, co-treatment with LAQ824 and Apo-2L/TRAIL induced more apoptosis than treatment with either agent alone. These data are similar to those derived from HL-60/Bcl-2 cells, in that the resistance of primary AML cells to Apo-2L/TRAIL-induced apoptosis could be overcome by co-treatment with LAQ824 plus Apo-2L/TRAIL. Based on the availability adequate sample, we also determined the effect of LAQ824 on the determinants of Apo-2L/TRAIL-induced DISC. As shown in FIG. 11A, in a representative sample of primary AML blasts, and similar to the cultured acute leukemia cells, treatment with 100 or 250 nM LAQ824 for 24 hours induced the acetylation of histones H3 and H4 (not shown). LAQ824 treatment also increased DR4 and DR5 levels, as well as down regulated the levels of FLIPL and c-FLIPS (FIG. 11A). Corresponding to the increase in the intracellular levels of DR5 determined by Western analysis, treatment of the primary AML sample with 100 and 250 nM LAQ824 also increased the DR5 expression on the cell membrane, as determined by flow cytometry, from a baseline of 17.5% to 33.2 and 62.4% of cells, respectively (FIG. 11B).

CONCLUSION

Consistent with the previous reports focused on the anti-leukemia activity of the other HDIs (37, 39-41), the present invention demonstrates that treatment with LAQ824 also induces p21 and p27, inhibits cell cycle progression and triggers caspase-dependent intrinsic pathway of apoptosis of acute myeloid and lymphoid leukemia cells. In addition, the present invention shows for the first time that treatment with LAQ824 can modulate the expression of the key determinants of Apo-2L/TRAIL-induced apoptosis. LAQ824 treatment results in increased Apo-2L/TRAIL-induced DISC assembly and activity in acute leukemia cells, which involves auto-activation of caspase-8 by proteolysis. Additionally, by down-modulating the expressions of the key anti-apoptotic Bcl-2 and IAP family members, LAQ824 treatment further facilitates both the mitochondria-initiated and common pathway of apoptosis, downstream of Apo-2L/TRAIL-induced processing and activation of caspase-8 followed by BID.

A number of preclinical studies utilizing a variety of tumor models have shown that pre-treatment with chemotherapeutic agents, including DNA damaging drugs, e.g., topoisomerase inhibitors, antimetabolites and antimicrotubule agents, increase the expression of DR4 and DR5 and enhance Apo-2L/TRAIL-induced DISC activity and apoptosis. Consistent with these findings, LAQ824 mediated induction of DR5 and DR4 levels is associated with increased Apo-2L/TRAIL-induced DISC assembly and activity. However, it has not been possible to detect any effect of LAQ824 on the expression of DcR1 and DcR2, suggesting a lack of their role in LAQ824-mediated enhancement of Apo-2L/TRAIL-induced DISC assembly and activity in acute leukemia cells. This is consistent with the prior reports that failed to show any correlation between DcR expression and Apo-2L/TRAIL sensitivity. Although LAQ824 treatment increased the intracellular levels of Apo-2L/TRAIL, its surface expression was not increased, discounting its role in LAQ824-induced apoptosis of acute leukemia cells. In a previous report, treatment of neuroblastoma cells with a hybrid polar HDI M-carboxycinnamic acid bishydroxamide (CBHA) was shown to induce the expression of Fas and Fas ligand within 12 hours. However, neither the mechanism underlying this effect nor its impact on Fas ligand-induced apoptosis was determined. In contrast, present studies demonstrate that treatment with LAQ824 increases the mRNA levels of DR4 and DR5. With respect to DR5, this was due to LAQ824-induced increased association of DR5 promoter with acetylated histones, which facilitates the binding of a trans-activator to the DR5 promoter, as is the case with the p21 promoter. LAQ824 also induces the acetylation of lysine residues on the trans-activator, thereby increasing its DNA binding. This is supported by the acetylation of specific lysine residues affecting the DNA binding and/or activity of p53, GATA-1 and E2F1. There is also the stability of DR4 and DR5 mRNA as increased by treatment with LAQ824, which adds to the increase in the mRNA levels of DR4 and DR5.

In a recent report the histone deacetylase inhibitor Depsipeptide was shown to down regulate c-FLIP, which was associated with caspase-8 and caspase-3 activation and apoptosis of CLL cells. Consistent with this observation, present studies also showed that LAQ824 treatment decreased the mRNA transcript and protein levels of c-FLIP. Importantly, LAQ824 mediated increase in DR4 and DR5, and the decline in c-FLIP were also observed in a primary sample of AML blasts (FIG. 11). Although the precise underlying mechanism was not established, this effect may be playing an important role in the sensitizing effect of LAQ824 on Apo-2L/TRAIL-induced DISC activity and apoptosis. This inference is strongly supported by the previous reports demonstrating that c-FLIP is a potent inhibitor of Apo-2L/TRAIL-induced DISC activity and apoptosis. In addition, down-modulation of c-FLIP levels has been shown to increase Apo-2L/TRAIL-induced processing of caspase-8 and apoptosis in human leukemia and cancer cells. Furthermore, the finding that the sensitizing effect of LAQ824 on Apo-2L/TRAIL-induced apoptosis was attenuated in Jurkat-DN FADD versus Jurkat-Zeo cells also strongly supports this conclusion. Regardless, present studies indicate that co-treatment with LAQ824 may overcome resistance to Apo-2L/TRAIL-induced apoptosis due to high c-FLIP levels in acute leukemia blasts.

The inventive method also clearly demonstrates that treatment with LAQ824 attenuated the protein levels of Bcl-$x_L$ and Bcl-2, which was associated with greater accumulation of the pro-death molecules, i.e., cytochrome c, Smac and Omi, in the cytosol of the cells treated with LAQ824 and Apo-2L/TRAIL versus those treated with Apo-2L/TRAIL alone. Although the precise mechanism responsible for the attenuation of Bcl-$x_L$ and Bcl-2 by LAQ824 has not been elucidated, present studies show that the attenuation was not dependent on caspase or proteasome activity. Regardless, the attenuation of Bcl-$x_L$ and Bcl-2, and the resulting greater cytosolic accumulation of Smac and Omi, most likely contributes to the sensitizing effect of LAQ824 on Apo-2L/TRAIL-induced apoptosis. This conclusion is supported by the finding that apoptosis induced by co-treatment with LAQ824 and Apo-2L/TRAIL is partially inhibited in HL-60/Bcl-2 versus HL-60/Neo cells (FIG. 10A). Several previous reports have also highlighted that Bcl-2 (or Bcl-$x_L$) overexpression inhibits Apo-2L/TRAIL-induced mitochondrial pathway of apoptosis. Therefore, conversely, abrogation of Bcl-2 (or Bcl-$x_L$) levels and activity would lead to increased Apo-2L/TRAIL-induced apoptosis, as has also been shown in this report. Furthermore, three recent studies have highlighted the role of Bax, which abrogates Bcl-2 and Bcl-$x_L$ activity, in Apo-2L/TRAIL-induced apoptosis. Taken together, these studies support the conclusion that attenuation of the mitochondria based anti-apoptotic molecules is likely to contribute to the enhancement of Apo-2L/TRAIL-induced apoptosis.

In addition to promoting the activity of the Apaf-1 mediated 'apoptosome' by increasing the cytosolic accumulation of cytochrome c, treatment with LAQ824 and Apo-2L/TRAIL also resulted in increased accumulation of Smac and Omi, which would exert anti-IAP effects and further potentiate Apo-2L/TRAIL-induced apoptosis. Since LAQ824 treatment alone attenuated XIAP levels (FIGS. 3B and 3C), not surprisingly, the combined treatment with LAQ824 and Apo-2L/TRAIL was associated with increased attenuation of XIAP. This is consistent with the recent reports that the accumulation of Omi, a serine protease, into the cytosol during Apo-2L/TRAIL-induced apoptosis is involved in the processing of XIAP. Previous reports have indicated that increased expression of XIAP and survivin is common and associated with poor clinical outcome in acute leukemia; Therefore, the combined treatment with LAQ824 and Apo-2L/TRAIL would be an attractive treatment strategy to test against acute leukemia, especially where resistance to apoptosis in the leukemia blasts is due to overexpression of Bcl-2 and/or LAP family of proteins. Although the preliminary data derived from six primary AML samples presented in Table 1, supports this view by indicating that combined treatment with LAQ824 and Apo-2L/TRAIL is superior to treatment with either agent alone, the expressions of XIAP and survivin were not studied in these samples.

In summary, due to the poor long-term clinical outcome in the adult patients with several forms of acute leukemia novel treatment strategies are needed to overcome resistance and sensitize the leukemia blasts to the extrinsic and intrinsic pathway of apoptosis. Treatment with LAQ824 and Apo-2L/TRAIL alone has been recognized to induce apoptosis of leukemia blasts but intrinsic mechanisms of resistance limit the antileukemia activity of either agent when administered alone. The inventive method overcomes the resistance to current apoptosis inducing treatments demonstrated by AML and CML-BC cells by concomitantly administering Apo-2L/TRAIL with the histone deacetylase inhibitor LAQ824.

FIG. 12 depicts the clinical application of the inventive method. After a patient is diagnosed with Leukemia 10 the target cells are identified 20. The target cells are then concomitantly treated with a therapeutic amount of TRAIL and a histone deacetylase inhibitor 30. After treatment the patient is monitored to determine the target cell's resistance to the treatment and the possibility of relapse 40.

The pharmaceutical compositions of the subject invention can be formulated according to known methods for preparing pharmaceutically and therapeutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin EW [1995] Easton Pa., Mack Publishing Company, $19^{th}$ ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question. The pharmaceutical composition can be adapted for various forms of administration. Administration can be continuous or at distinct intervals as can be determined by a person skilled in the art.

The administration of TRAIL and LAQ824 is dosed in accordance with good medical practice, taking into account the clinical condition of the individual patient, the site and method of administration, scheduling of administration, patient age, sex, body weight, and other factors known to medical practitioners.

The therapeutically "effective amount" for purposes herein is thus determined by such considerations as are known in the art.

TABLE 1

| | % of apoptosis | | | |
|---|---|---|---|---|
| Pts: | Control | LAQ824 | Apo-2L/ TRAIL | LAQ824 + Apo-2L/TRAIL |
| 1 | 7.2 | 14.5 | 7.6 | 27.2 |
| 2 | 12.4 | 29.5 | 14.0 | 44.5 |
| 3 | 8.0 | 22.9 | 8.6 | 39.4 |
| 4 | 10.1 | 27.9 | 11.0 | 42.3 |
| 5 | 6.3 | 57.8 | 6.8 | 64.9 |
| 6 | 7.2 | 7.9 | 8.1 | 25.4 |

Legend:
Co-treatment with LAQ824 enhances Apo-2/L TRAIL-induced apoptosis. Primary AML cells from six patients were treated with LAQ824 (100 nM) and/or Apo-2/L TRAIL (100 ng/ml) for 24 hours. Following this, percentage of apoptotic cells was determined by annexin V staining and flow cytometry. Values represent the mean of two experiments performed in duplicate.

TABLE 2

| REAGENT | PROVIDED BY |
|---|---|
| LAQ824 | Novartis Pharmaceuticals Inc. (East Hanover, NJ) |
| recombinant human trimeric form of Apo-2L/ TRAIL | Genentech, Inc. (South San Francisco, CA) |
| Anti-Bid and anti-Smac/DIABLO antibodies | Dr. Xiaodong Wang of the University of Texas, Southwestern School of Medicine (TX) |
| Monoclonal anti-XIAP antibody | Boehringer Mannheim (Indianapolis, IN) |
| Polyclonal anti-PARP and monoclonal anti-cIAP-1, caspase-9 and caspase-3 antibodies | Pharmingen Inc. (San Diego, CA) |
| Polyclonal anti-caspase-8 antibody | Upstate Biotechnology (Lake Placid, NY) |
| monoclonal anti-survivin | Alpha Diagnostic (San Antonio, TX) |
| DR4 antibody | Alexis Corp. (San Diego, CA). |
| Polyclonal anti-DR5 | Cayman Chemicals Co. (Ann Arbor, MI) |
| Monoclonal anti-cytochrome oxidase-2 antibody | Molecular Probe (Eugene, OR) |
| z-VAD-FMK and LLnL | Calbiochem (San Diego, CA) |
| Jurkat T cell leukemia and SKW6.4 B lymphoblast | American Tissue Culture Collection (Manassas, VA) |

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for the treatment of leukemia comprising the steps of:

contacting a target cell with a therapeutic amount of Apo-2L/TRAIL; and concomitantly contacting the target cell with a therapeutic amount of LAQ824.

2. The method of claim 1 wherein the leukemia is human acute myeloid leukemia.

3. The method of claim 1 wherein the leukemia is chronic myelogenous leukemia in blast crisis.

4. A pharmaceutical composition for treating leukemia, the composition comprising LAQ824, Apo-2L/TRAIL, and a pharmaceutically acceptable carrier.

5. A method of treating leukemia, the method comprising administering to a patient in need of such treatment a pharmaceutical composition comprising LAQ824, Apo-2L/TRAIL, and a pharmaceutically acceptable carrier.

* * * * *